US006859281B2

(12) United States Patent
Hovinen et al.

(10) Patent No.: US 6,859,281 B2
(45) Date of Patent: Feb. 22, 2005

(54) METHOD FOR DETERMINING ION CONCENTRATION AND ENERGY OF SHALLOW JUNCTION IMPLANTS

(75) Inventors: Minna Hovinen, Maple Grove, MN (US); Jon Opsal, Livermore, CA (US)

(73) Assignee: Therma-Wave, Inc., Fremont, CA (US)

( * ) Notice: Subject to any disclaimer, the term of this patent is extended or adjusted under 35 U.S.C. 154(b) by 0 days.

(21) Appl. No.: 10/689,332

(22) Filed: Oct. 20, 2003

(65) Prior Publication Data

US 2004/0085538 A1 May 6, 2004

Related U.S. Application Data

(62) Division of application No. 10/341,225, filed on Jan. 13, 2003, now Pat. No. 6,665,071, which is a division of application No. 09/884,262, filed on Jun. 19, 2001, now Pat. No. 6,532,070.
(60) Provisional application No. 60/218,594, filed on Jul. 17, 2000.

(51) Int. Cl.[7] .............................................. G01N 21/41
(52) U.S. Cl. ..................... 356/369; 356/370; 356/376; 356/371
(58) Field of Search ............................... 356/369, 370, 356/376, 371, 381–382, 432 T, 432, 433

(56) References Cited

U.S. PATENT DOCUMENTS

| 4,522,510 A | 6/1985 | Rosencwaig et al. ........... 374/7 |
| 4,636,088 A | 1/1987 | Rosencwaig et al. ........... 374/5 |
| 4,710,030 A | 12/1987 | Tauc et al. .................. 356/432 |
| 4,854,710 A | 8/1989 | Opsal et al. ................. 356/432 |
| 4,999,014 A | 3/1991 | Gold et al. .................. 356/382 |
| 5,074,669 A | 12/1991 | Opsal ......................... 356/445 |
| 5,181,080 A | 1/1993 | Fanton et al. ............... 356/381 |
| 5,298,970 A | 3/1994 | Takamatsu et al. .......... 356/349 |
| 5,973,787 A | 10/1999 | Aspnes et al. .............. 356/369 |
| 5,978,074 A | 11/1999 | Opsal et al. ................ 356/72 |
| 6,052,188 A | 4/2000 | Fluckiger et al. ........... 356/369 |
| 6,081,330 A | 6/2000 | Nelson et al. .............. 356/318 |
| 6,268,916 B1 | 7/2001 | Lee et al. .................... 356/369 |
| 6,512,815 B2 | 1/2003 | Opsal et al. ................. 378/89 |
| 6,535,285 B1 | 3/2003 | Opsal et al. ................ 356/369 |

FOREIGN PATENT DOCUMENTS

| WO | WO 99/02970 | 1/1999 | .......... G01N/21/21 |
| WO | WO 00/68656 | 11/2000 | ............. G01J/4/00 |

OTHER PUBLICATIONS

L. Zhou et al., "Use of a New Thermal Wave Technology for Ultra–Shallow Junction Implant Monitoring," *Proceedings of the X International Conference on Ion Implantation Technology*, Jun. 1998, Kyoto (Japan), pp. 1–4.

A. Salnick et al., "Quantitative Photothermal Characterization of Ion–Implanted Layers in Si," *25th Review of Progress in QNDE*, Snowbird (Utah), Jul. 19–24, 1998, pp. 1–15.

U.S. Appl. No. 09/499,974, filed Feb. 8, 2000, entitled "Combination Thermal Wave and Optical Spectroscopy Measurement System,". (5 drawing pages included) by Jon Opsal et al., 29 pages in length.

*Primary Examiner*—Mohammad Sikder
(74) *Attorney, Agent, or Firm*—Stallman & Pollock LLP

(57) ABSTRACT

A method is disclosed for measuring the dose and energy level of ion implants forming a shallow junction in a semiconductor sample. In the method, two independent measurements of the sample are made. The first measurement monitors the response of the sample to periodic excitation. In the illustrated embodiment, the modulated optical reflectivity of a reflected probe beam is monitored to provide information related to the generation of thermal and/or plasma waves in the sample. A second spectroscopic measurement is also performed. This measurement could be either a spectroscopic reflectometry measurement or a spectroscopic ellipsometry measurement. The data from the two measurements are combined in a manner to yield information about both the dose (concentration) of the dopants as well as the energy used to inject the dopants in the semiconductor lattice. The method will useful in controlling the formation of shallow junctions.

4 Claims, 4 Drawing Sheets

METHOD FOR DETERMINING ION CONCENTRATION AND ENERGY OF SHALLOW JUNCTION IMPLANTS

PRIORITY

This application is a divisional of U.S. patent application Ser. No. 10/341,225 filed Jan. 13, 2003 now U.S. Pat. No. 6,665,071, which was in turn a divisional of U.S. patent application Ser. No. 09/884,262, filed Jun. 19, 2001 now U.S. Pat. No 6,532,070, which claims priority from provisional application Ser. No. 60/218,594, filed Jul. 17, 2000.

TECHNICAL FIELD

The subject invention relates to a method for evaluating the characteristics of shallow junctions formed on semiconductor wafers. More specifically, the invention relates to the optical inspection of shallow junctions and the determination of energy and dose of the implants used to create the shallow junction.

BACKGROUND OF THE INVENTION

The use of optical inspection methods to evaluate ion implants has been well known for some time. Successful measurements have been made with equipment in which an intensity modulated pump beam is used to periodically excite a small spot on the sample surface. The effects of the periodic excitation, which tend to generate thermal and/or plasma waves, are monitored with an optical probe beam. One such effect is periodic surface displacements which can be measured through interferometry or by monitoring periodic angular displacements of the probe beam. Another effect is periodic changes to the reflectivity of the sample which are monitored by measuring periodic changes in the power of a reflected probe beam. Further details of such systems can be found in U.S. Pat. Nos. 4,522,510; 4,636,088; and 4,854,710.

These systems were capable of adequately measuring a relatively wide range of ion implant dosage levels. In order to improve sensitivity to higher doses, various other approaches have been taken. In one approach, the steady state reflectivity of one or more single wavelength probe beams was measured and combined with the thermal wave data to reduce ambiguities. Such an approach is described in U.S. Pat. No. 5,074,669.

Additional efforts to increase the measurement capabilities of such systems included varying the distance between the pump and probe beam spots; varying the modulation frequency of the pump source; and combining the thermal wave data with other measured data such as from spectroscopic reflectometry or ellipsometry. Such efforts are described in U.S. Pat. No. 5,978,074 and copending U.S. patent application Ser. No. 09/499,974, filed Feb. 8, 2000. All of the above cited patents and patent applications are incorporated by reference.

The above described techniques do not function to measure ion concentration directly, rather, they measure the damage done to the crystal lattice structure by the implanted ions. Variations in dosage level produce different levels of damage which can be detected by the thermal wave measurements. Variations in the energy used to implant the ions also affects the extent of damage to the lattice. As the energy level is increased, the ions are driven deeper into the lattice and the damage is more extensive.

It would be desirable to develop a measurement method which could separate out the contributions of the dose and energy levels of the implants to the damage of the wafer. In this way, the process used to create the implants can be better controlled. Such a measurement would extremely useful in the fabrication of shallow junctions in semiconductors.

More specifically, in the effort to achieve further miniaturization of semiconductor devices, the junctions dimensions must be reduced, both in width and depth. According to the 1999 SIA international roadmap, the next technology node to be achieved in two years is characterized by a lateral channel length of 130 nm, which means that the vertical drain and source pn-junction depths have to be shallower than 100 nm. Low energy ion implantation (<5 keV) has been developed to achieve these ultra-shallow junction depths, The need to create these shallow junctions requires unprecedented control of the ion implantation process. Any unexpected variations in either dosage level or energy of the implant can result in the failure of the circuit. Therefore, it would be highly desirable to adapt the prior measurement approaches to evaluate both dosage level (ion concentration) and the energy of the implants.

Research experiments have concentrated on using destructive methods such as secondary ion mass spectrometry (SIMS) transmission electron microscopy (TEM) and spreading resistance depth profiling. Some attempts for non-destructive analysis have been made with ion scattering and spectroscopic ellipsometry, while the non-destructive thermal wave methods have demonstrated low sensitivity for implants below 5 keV.

Most SIMS equipment have a physical limitation for accurate depth profiling of ultra-shallow junctions. A transient region down to 100 Å depth is typically formed at the oxygen bombarded surface due to ionization effects at the oxidized silicon surface. Special test samples are typically required with a silicon capping layer to avoid the surface effect. TEM imaging involves tedious cross-sectional sample preparation, but is generally considered the most accurate way to measure the crystalline damage depth. Spreading resistance depth profiling requires an electrical contact to be established to the wafer surface. Specialized probe conditioning and sample preparation are needed for reliable measurement of ultra-shallow junctions and currently only a few labs have succeeded in these analyses. The ion scattering methods are restricted to give the depth distribution of the displaced silicon atoms only and have been found to lack the sensitivity to detect defects at levels which are important in device operation. Spectroscopic ellipsometry has been used with simple 1–2 layer models with effective medium approach for layer mixing, which complicates the analyses as separate recipes are needed for high and low (<2.5 keV) ion implants.

SUMMARY OF THE INVENTION

In accordance with the subject invention, these problems are overcome by combining the outputs from both a thermal wave type measurement and a spectroscopic measurement, either broadband spectroscopy (reflectometry) or broadband ellipsometry.

This approach can provide accurate depth profiling of both the crystalline damage and the implanted ion distribution right after the implantation, before annealing.

In the preferred embodiment, the sample is periodically excited using an intensity modulated pump beam. A separate probe beam monitors the effects of the periodic excitation. As noted above, this can include effects such as the a) modulated optical reflectivity (MOR); b) vertical displacements (interferometry); c) angular displacements of a displaced probe beam; and d) periodic ellipsometric effects. (See, for example, PCT WO 00/68656, incorporated herein by reference.) The selected measurements produce first output signals that are supplied to a processor.

In accordance with the subject invention, a second, spectroscopic measurement is made within the same region of the sample. This spectroscopic measurement can be a reflectometry measurement at multiple wavelengths or a spectroscopic ellipsometry measurement at multiple wavelengths. The selected measurements produce second output signals that are supplied to a processor.

The first and second signals are combined in the processor to evaluate both the dosage level and the energy of the implant. More specifically, a theoretical model is set up which corresponds to the actual sample, including a substrate and the shallow junction. The model includes various characteristics of the material, for example, thickness of the damaged region, index of refraction, and extinction coefficient. The model is typically seeded with initial parameters of the sample. Using the Fresnel equations, calculations are performed to determine expected measurement data if the modeled sample actually existed and was measured. This calculated data is then compared to the actual measured data. Differences between the calculated data and the actual measured data are then used to vary the expected characteristics of the sample of the model in an iterative regression process for determining the actual composition of the sample, including the dosage level and energy of the implant.

Depending upon the particular sample, additional measurements may also be made to improve the analysis. For example, it may be desirable to use both a reflectometry measurement and a spectroscopic ellipsometry method to produce enough data to generate an unambiguous result. Further measurements which be used include the assignees propriety Beam Profile Reflectometry™ and Beam Profile Ellipsometry™ systems. Details about such systems can be found in U.S. Pat. Nos. 4,999,014, and 5,181,080, incorporated herein by reference. The assignee herein sells a metrology tool under the name Opti-Probe which combines a number of measurement techniques on a single platform. Such techniques include: Spectroscopic Reflectometry, Spectroscopic Ellipsometry, Beam Profile Reflectometry™ Beam Profile Ellipsometry™ and single wavelength ellipsometry (Absolute Ellipsometer™). A basic description of this tool can be found in WO 99/02970, incorporated herein by reference.

Further objects and advantages of the subject invention will become apparent with the following detailed description, taken in conjunction with the drawings, in which:

DETAILED DESCRIPTION OF THE PREFERRED EMBODIMENTS

Figure 1:
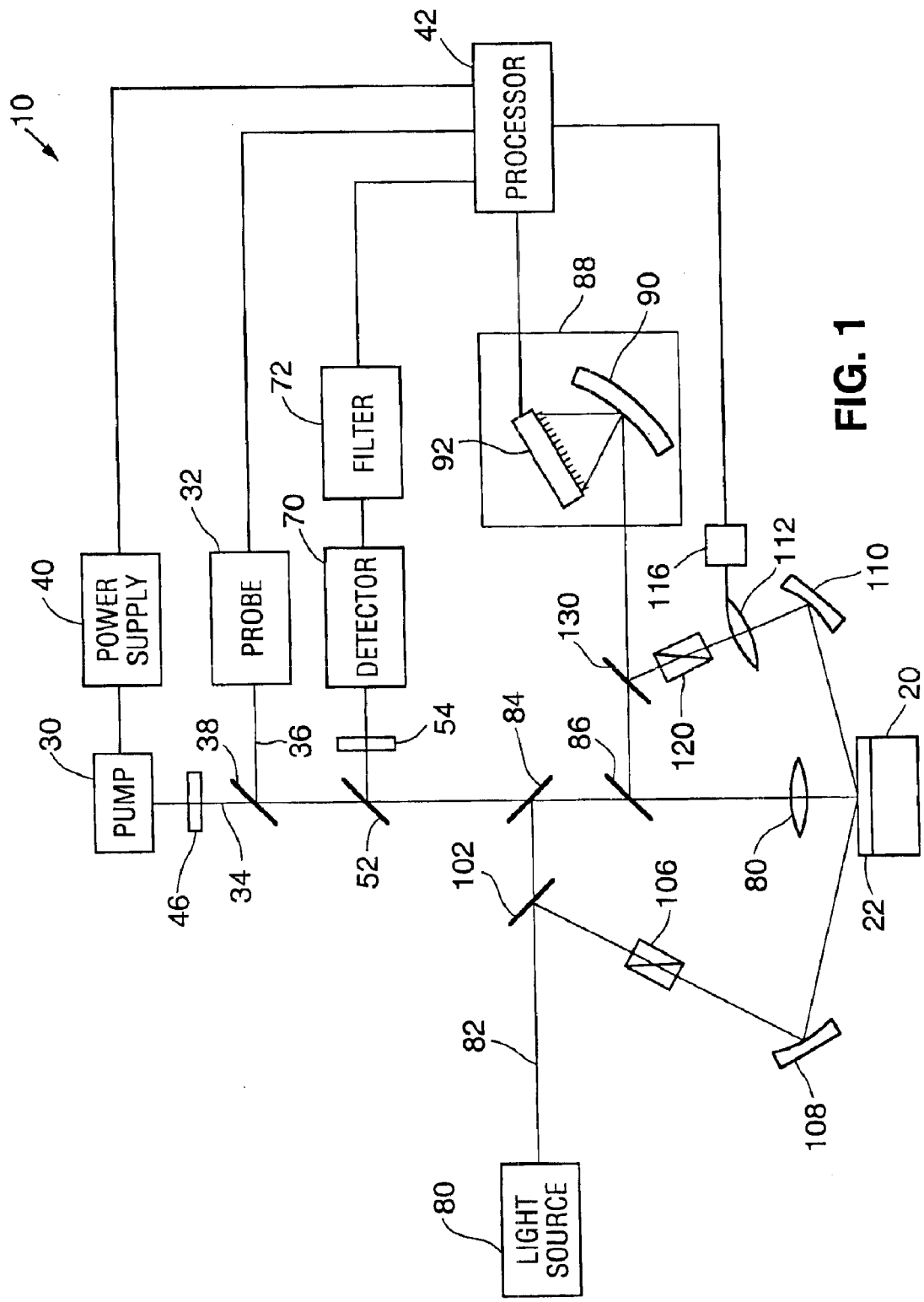
FIG. 1 is a schematic diagram of the apparatus for carrying out the methods of the subject invention.

FIG. 1 is a simplified diagram of the basic components of an apparatus 10 which can be used to take the measurements useful in applying the methods of the subject invention. The apparatus is particularly suited for measuring characteristics of semiconductor wafers 20. In one important aspect of the invention, the device is used to evaluate ion implantations in the wafer. In particular, the device is used to characterize both the dose and energy levels of the implanted ions.

In accordance with the subject invention, the apparatus includes a first measurement system for generating thermal and/or plasma wavers and monitoring the propagation of these waves in the sample. This portion of the system includes a pump laser 30 for exciting the sample and a probe laser 32 for monitoring the sample. Gas, solid state or semiconductor lasers can be used. As described in the assignee's earlier patents, other means for exciting the sample can include different sources of electromagnetic radiation or particle beams such as from an electron gun. In the preferred embodiment, semiconductor lasers are selected for both the pump and probe lasers due to their reliability and long life. In the illustrated embodiment, pump laser 30 generates a near infrared output beam 34 at 780 nm while probe laser 32 generates a visible output beam 36 at 673 nm. The outputs of the two lasers are linearly polarized. The beams are combined with a dichroic mirror 38. It is also possible to use two lasers with similar wavelengths and rely on polarization discrimination for beam combining and splitting.

Pump laser 30 is connected to a power supply 40 which is under the control of a processor 42. The output beam of laser 30 is intensity modulated through the output of power supply 40. The modulation frequency has a range running from 100 KHz to 100 MHz. In the preferred embodiment, the modulation frequency can be set up to 125 MHz. As described in the above cited patents, if an ion laser is used to generate the pump beam, the intensity modulation can be achieved by a separate acousto-optic modulator. Prior to reaching the beam combining mirror 36, the probe beam 34 passes through a tracker 46. Tracker 46 is used to control the lateral position of beam 34 with respect to the probe beam. In some measurements, the two beams will be positioned so that the spots will overlap on the sample surface. In addition, measurements can be taken at various spacings between the pump and probe beam spots. Measurements at different spatial separations are discussed in greater detail in U.S. Pat. No. 5,978,074.

The beams are directed down to the sample 20 through a microscope objective 50. Objective 50 has a high n.a., on the order of 0.9, and is capable of focusing the beam to a spot size on the order of a few microns and preferably close to one micron in diameter. The spacing between the objective and the sample is controlled by an autofocus system not shown herein but described in U.S. Pat. No. 5,978,074.

The returning reflected beams 34 and 36 are reflected by beam splitter 52. A filter 54 is provided to remove the pump beam light 34 allowing the probe beam light to fall on the photodetector 70. Detector 70 provides an output signal which is proportional to the power of the reflected probe beam 36. Detector 70 is arranged to be underfilled so that its output can be insensitive to any changes in beam diameter or position. In the preferred embodiment, detector 70 is a quad cell generating four separate outputs. When used to measure reflected beam power, the output of all four quadrants are summed. As described in U.S. Pat. No. 5,978,074, the apparatus can also be operated to measure beam deflection. In the latter case, the output of one adjacent pair of quadrants is summed and subtracted from the sum of the remaining pair of quadrants.

The output of the photodetector 70 is passed through a low pass filter 72 before reaching processor 42. One function of filter 72 is to pass a signal to the processor 42 proportional to the DC power of the reflected probe. A portion of filter 72 also functions to isolate the changes in power of the reflected probe beam which are synchronous with the pump beam modulation frequency. In the preferred embodiment, the filter 72 includes a lock-in detector for monitoring the magnitude and phase of the periodic reflectivity signal. Because the modulation frequency of the pump laser can be so high, it is preferable to provide an initial down-mixing stage for reducing the frequency of detection. Further details of the preferred filter and alternatives are described in U.S. Pat. No. 5,978,074. For example, it would be possible to use a modulated pump beam to obtain an optically heterodyned signal as described in U.S. Pat. No. 5,206,710, incorporated herein by reference.

To insure proper repeatability of the measurements, the signals must be normalized in the processor. As noted above, the DC reflectivity of the probe beam is derived from detector 70. In addition, the DC output powers of the pump and probe lasers are monitored by incident power detectors (not shown) and provided to the processor. The signals are further normalized by taking a measurement of the power of the pump beam 34 after it has been reflected by another detector (not shown). This measurement is used to determine the amount of pump energy which has been absorbed in the sample. The DC signal for both the incident pump and probe beam powers as well as the reflected beam powers are used to correct for laser intensity fluctuations and absorption and reflection variations in the samples. In addition, the signals can be used to help calculate sample parameters.

In accordance with the subject invention, in addition to the thermal wave measurement system, a separate spectroscopic measurement system is also included. This additional system includes a polychromatic or broad band light source 80. Light source 80 can be defined by a single broadband lamp, such as a xenon arc lamp. Alternatively, the light source could be defined by two or more lamps such as a xenon arc lamp to cover of the visible light ranges and a separate deuterium lamp to cover the ultraviolet ranges.

The output from light source 80 is a polychromatic probe the beam 82. The beam can be redirected by a splitter 84 towards the sample. The beam 82 is focused onto the sample by microscope objective 50. The reflected beam is redirected by splitter 86 to a spectrometer 88. The spectrometer can be of any type commonly known and used in the prior art. In the illustrated embodiment, the spectrometer includes a curved grating 90 which functions to angularly spread the beam as a function of wavelengths. A photodetector 92 is provided for measuring the beam. Photodetector 92 is typically a photodiode array with different wavelengths or colors falling on each element in the array. Other alternative detectors would include a CCD camera or photomultiplier. It should be noted that it is within the scope of this invention to use a monochrometer and obtain measurements serially (one wavelength at a time) using a single detector element. The output of detector 92 is supplied to the processor 42. When the polychromatic light beam 82 follows the path discussed above, the output of detector 92 would correspond to the reflectance of the sample.

In accordance with the subject invention, polychromatic light beam 82 can also be used to obtain spectroscopic ellipsometric measurements. In order to obtain spectroscopic ellipsometric measurements, a beam splitter 102 can be placed in the path of the polychromatic light beam 82. Beams splitter 102 redirects the beam through polarizer 106 to create a known polarization state. Polarizer 106 can be a linear polarizer made from a quartz Rochon prism. The polarized probe beam is focused onto the sample 20 by a curved mirror 108. The beam strikes the sample at an angle on the order of 70 degrees to the normal to maximize sensitivity. Based upon well-known ellipsometric principles, the reflected beam will generally have a mixed linear and circular polarization state after interacting with the sample, as compared to the linear polarization state of the incoming beam. The reflected beam is redirected by mirror 110 through a rotating compensator 112. Compensator 112 introduces a relative phase delay or phase retardation between a pair of mutually orthogonal polarized optical beam components. The amount of phase retardation is a function of the wavelength, the dispersion characteristics of the material used to form the compensator and the thickness of the compensator. The compensator is rotated by motor 116 at an angular velocity w about an axis substantially parallel to the propagation direction of the beam. In the preferred embodiments, compensator 112 is a bi-plate compensator constructed of two parallel plates of anisotropic (usually birefringent) material, such as quartz crystals of opposite handedness, where the fast axes of the two plates are perpendicular to each other and the thicknesses are nearly equal, differing only by enough to realize a net first-order retardation over the wavelength range of interest.

After passing through the compensator 112, the beam interacts with the analyzer 120. Analyzer 120 service to mix a polarization states of the beam. In this embodiment, analyzer 120 is another linear polarizer. The rotating compensator spectroscopic ellipsometer illustrated herein is described in greater detail in U.S. Pat. No. 5,973,787 assigned to the same assignee and incorporated herein by reference. While a rotating compensator ellipsometer is disclosed, the scope of the subject invention is intended to include any of the other conventional spectroscopic ellipsometer configurations. These would include rotating analyzer systems as well as fixed element systems that rely on photoelastic modulators for retardation.

After the beam passes analyzer 120 it is reflected by beam splitter 130 and directed to the spectrometer 88. As noted above, grating 90 disperses the beam onto the array detector 92. The measured output from the spectrometer corresponds to the change in polarization state of the beam and from this information, the traditional ellipsometric parameters 105 and Δ can be derived.

The optical layout in FIG. 1 is intended to illustrate how both a thermal wave detection system and a spectroscopic detection system, and in particular, a spectroscopic ellipsometric system might be employed to obtain measurements at generally the same spot on the surface of the sample and in a near contemporaneous fashion. In this manner, the combination of the measurements results will produce a more accurate result. The combination of the two metrology devices in a single tool in addition to providing more accurate results provides economic benefits as well. For example, a single tool has a smaller footprint and therefore takes up less space in the semiconductor fab. By combining technologies in a single tool, costs can be reduced by eliminating duplicate subsystems such as wafer handlers and computers. Finally, the combination can simplify and streamline decision making since the information from the two measurement modalities can be coordinated instead of producing conflicting results which can occur if two separate devices were used.

While combining the technologies on a single tool will have advantages, it is within the scope of the method of the subject invention to obtain the measurements from two separate tools. The experiments described below were successfully performed using two separate, commercially available tools from the assignee. Specifically, the thermal/plasma wave measurements were obtained from a Therma-Probe 500 while the spectroscopic measurements were obtained from an Opti-Probe 5240. As noted above, the latter device includes additional measurement technologies that were also utilized in the experiments.

Experiments 200 mm diameter wafers were measured by thermal wave and spectroscopic tools. The thermal wave data gives an estimate of the total integrated crystalline damage in the sub-surface regions of the wafer. A pump laser with wavelength $\lambda=532$ nm was modulated at 1 MHz frequency and focused on the wafer surface in a 2 micron diameter spot. This is estimated to generate a thermal wave (TW) with a thermal diffusion length of about 5 microns propagating towards the thermal sinks in the sample. A probe laser at $\lambda=670$ nm was focused on the sample surface to measure the thermal wave induced changes in the reflectivity. The standard thermal wave technology was used to interpret the measured signals as the TW signal amplitude and the TW phase.

A commercial Opti-Probe tool was used to perform spectroscopic ellipsometry (SE), beam profile ellipsometry (BPE) and broad-band spectroscopic reflectometry (BB) measurements. The wavelength span of the spectroscopic measurements was from 190–820 nm while the single wavelength BPE at $\lambda=673$ nm, was used to help with the top oxide thickness measurement. A standard model consists of a top layer of silicon dioxide with the library optical dispersion relation and a stack of damaged silicon layers on top of the purely crystalline silicon substrate. The spectroscopic data were analyzed with the standard curve fitting algorithms allowing a multilayer, multiparameter fit simultaneously on the ellipsometry and reflectometry data. A model with a very good correlation between the fit and the experimental data (goodness of fit>0.98) was sought for each implant species. A dynamic model, with a damage layer dispersion fit, was developed to accommodate the change in silicon dispersion as a function of implant energy and dose. To estimate repeatability, 30 point precision data were taken by repeating the measurement at the same spot 30 times.

In addition to the dose sensitivity, the instrumental noise needs to be included in any analysis of implant monitoring capability. The dose sensitivity S in units of %-change in a monitoring parameter per %-change in ion dose can be estimated from $$S = \frac{(P_2 - P_1)/(P_2 + P_1)}{(D_2 - D_1)/(D_2 + D_1)}$$

where P refers to the monitoring parameter, D is the ion dose, and the subscript 1 and 2 refer to the samples in question. The 30 point precision results can be used to estimate the noise for each technology. The repeatability is defined as the standard deviation at 1-$\sigma$ and the percent notation %$\sigma$=1-$\sigma$/mean is used here. For each technology, the detection limit DL in %-change in dose can then be estimated from $$DL = \frac{\%\sigma}{S}$$

Two series of ultra shallow junction implants were studied. The energy and dose values of the arsenic and boron implants are summarized in Table I.

TABLE I

Characteristics of the arsenic and boron ultra shallow junction wafers.

| | Arsenic | | | Boron | |
|---|---|---|---|---|---|
| Wafer # | Energy (keV) | Dose (1/cm$^2$) | Wafer # | Energy (keV) | Dose (1/cm$^2$) |
| 1 | 5 | 1.10E+15 | 1 | 0.5 | 4.50E+14 |
| 2 | 5 | 9.00E+14 | 2 | 0.5 | 4.50E+14 |
| 3 | 5 | 5.50E+14 | 3 | 0.5 | 5.50E+14 |
| 4 | 5 | 4.50E+14 | 4 | 5 | 1.10E+15 |
| 5 | 5 | 4.50E+14 | 5 | 5 | 9.00E+14 |
| 6 | 2 | 9.00E+14 | 6 | 5 | 5.50E+14 |
| 7 | 2 | 5.50E+14 | 7 | 5 | 4.50E+14 |
| 8 | 2 | 4.50E+14 | 8 | 5 | 4.50E+14 |
| 9 | 2 | 4.50E+14 | 9 | 2 | 1.10E+15 |
| 10 | 1 | 5.50E+14 | 10 | 2 | 9.00E+14 |
| 11 | 1 | 4.50E+14 | 11 | 2 | 5.50E+14 |
| 12 | 1 | 4.50E+14 | 12 | 2 | 4.50E+14 |
| 13 | 1 | 9.00E+14 | 13 | 2 | 4.50E+14 |
| 14 | 1 | 1.10E+15 | 14 | 1 | 4.50E+14 |
| 15 | 0.5 | 4.50E+14 | 15 | 1 | 4.50E+14 |
| 16 | 0.5 | 4.50E+14 | 16 | 1 | 5.50E+14 |
| 17 | 0.5 | 5.50E+14 | 17 | 1 | 9.00E+14 |
| | | | 18 | 1 | 1.10E+15 |
| | | | 19 | 0.5 | 1.10E+15 |
| | | | 20 | 0.5 | 9.00E+14 |
| | | | 21 | 0.2 | 4.50E+14 |
| | | | 22 | 0.2 | 4.50E+14 |
| | | | 23 | 0.2 | 5.50E+14 |

Arsenic Ultra Shallow Junctions

Figure 2:
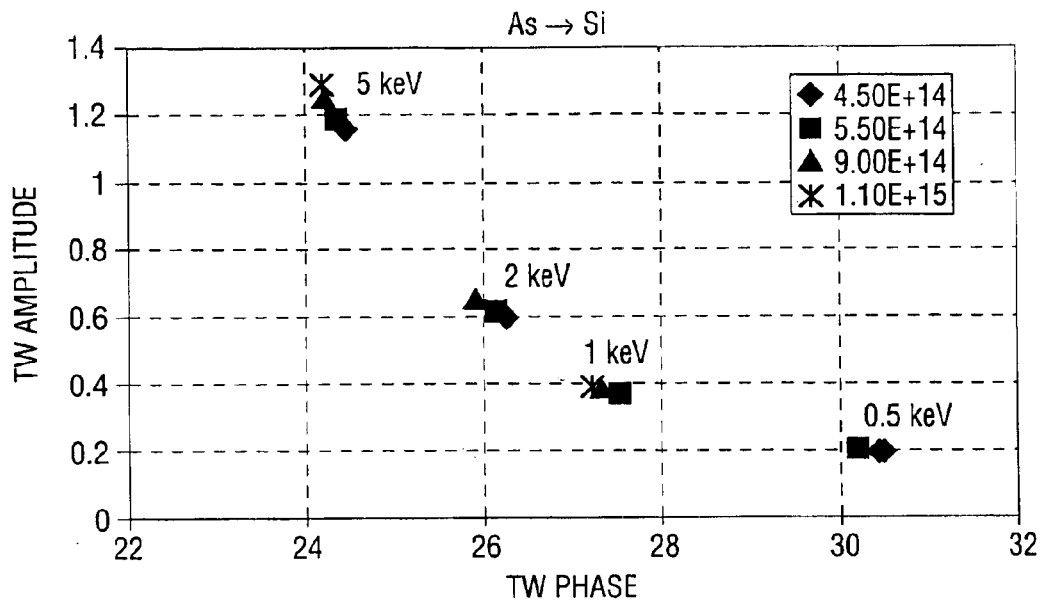
FIG. 2 is a thermal wave circle plot for arsenic shallow junction implants.

The 17 wafers had energy and dose values as given in Table I. FIG. 2 is a circle plot of TW amplitude versus TW phase. As can be seen from FIG. 2, the thermal wave method is able to distinguish between the various arsenic implant energies and doses. TW circle plots of known samples can thus be used as a calibration for arsenic ultra shallow junction implant monitoring.

Figure 3:
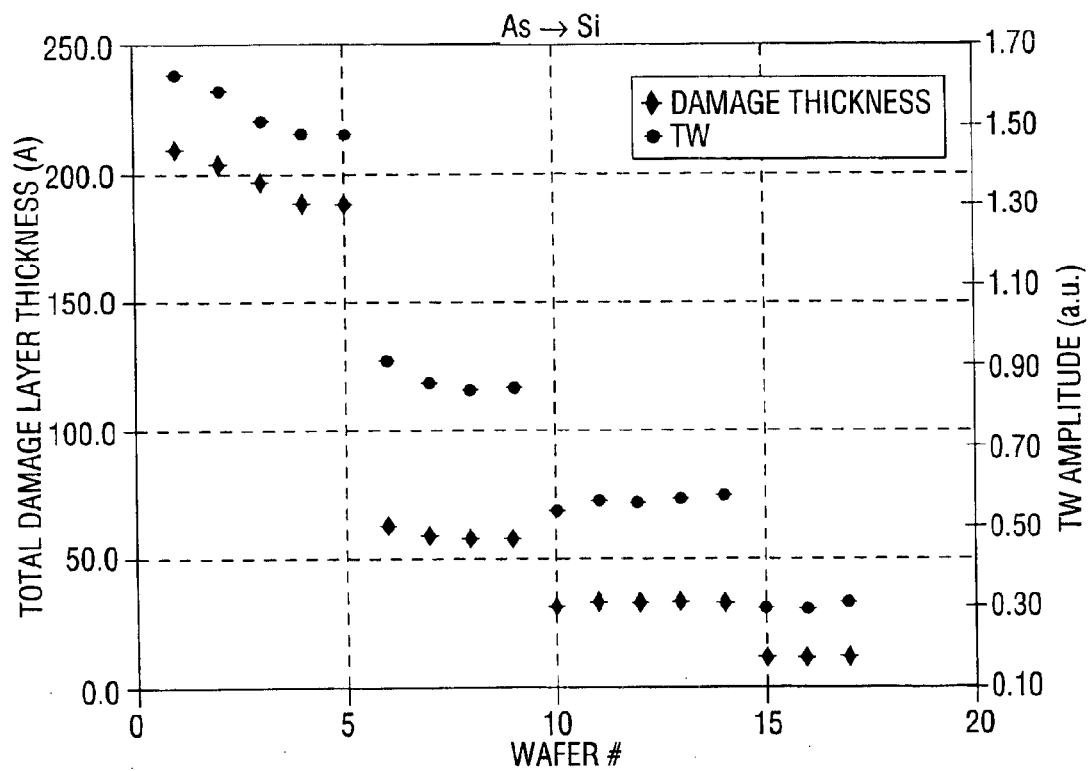
FIG. 3 illustrates the correlation between the spectroscopic and the thermal wave results for the arsenic shallow junction implants.

The spectroscopic data were measured with a commercial OptiProbe 5240 tool. A model with two damage layers under the top oxide was found to describe the whole range of Arsenic dopants with a single measurement recipe. The top layer was assumed to exhibit an optical dispersion close to amorphous silicon while the second damage layer was found to develop from more crystalline to more amorphous with increasing dose and energy. To avoid using a separate recipe for the high energy (>2 keV) implants, a dynamic solution was sought that allows the simultaneous fit of the optical dispersion of the bottom damage layer and the thickness of the three layers. The total thickness of the damage layers is increasing with the dopant energy and dose. FIG. 3 illustrates the correlation of the spectroscopic data and the thermal wave results and Table II gives the sensitivity and detectability results derived by the repeatability measurements. The error bar is the ±1-$\sigma$ limit of a 30 point precision measurement.

Thus, by combining the results of the spectroscopic analysis and the thermal wave data, we get thorough knowledge on the damage development as a function of arsenic ion dose and the ion energy. Both, the thermal wave method and the optical spectroscopy can be used independently to determine the extent of ion induced damage right after the implantation for arsenic shallow junctions. The thermal wave method is superior to spectroscopy with a 2–15% dose detection limit and <0.6% energy detection limit.

TABLE II

Arsenic implanted ultra shallow junctions: detection of energy and dose by the thermal wave and spectroscopic methods. S = sensitivity, DL = detection limit.

| Parameter | Condition | Thermal wave | | Spectroscopy | |
|---|---|---|---|---|---|
| Dose-range | Energy (keV) | S (%-per-%) | DL (%-dose) | S (%-per-%) | DL (%-dose) |
| 4.5e14–1.1e15 | 5.0 | 0.1056 | 1.98 | 0.1402 | 7.74 |
| 4.5e14–9.0e14 | 2.0 | 0.1137 | 2.02 | 0.1353 | 14.32 |
| 4.5e14–9.0e14 | 1.0 | 0.0972 | 6.39 | 0.0969 | 36.64 |
| 4.5e14–5.5e14 | 0.5 | 0.1822 | 15.83 | 0.2014 | 72.34 |
| Energy-range | Dose (1/cm$^2$) | S (%-per-%) | DL (%-energy) | S (%-per-%) | DL (%-energy) |
| 0.5–5 keV | 4.50E+14 | 0.7298 | 0.58 | 1.1699 | 2.06 |
| 1–5 keV | 5.50E+14 | 0.7262 | 0.45 | 1.1838 | 1.84 |
| 1–5 keV | 9.00E+14 | 0.6724 | 0.38 | 1.0719 | 1.40 |
| 1–5 keV | 1.10E+15 | 0.7138 | 0.50 | 0.5023 | 0.50 |

Figure 4:
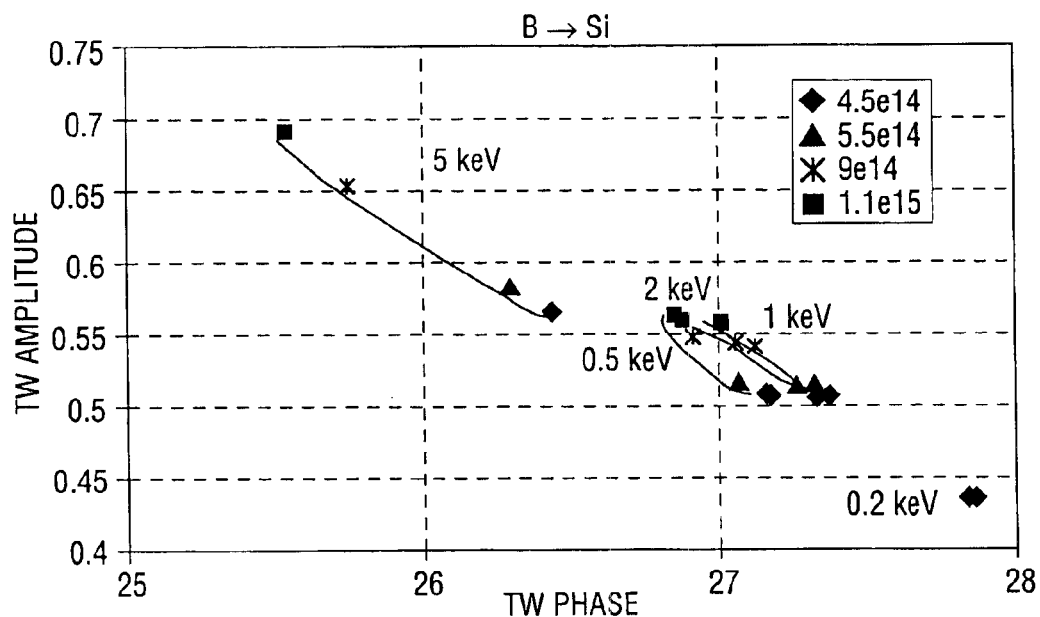
FIG. 4 is a thermal wave circle plot for boron ultra shallow junction implants.

Boron Ultra Shallow Junctions 23 wafers with the boron energy and dose values given in Table I were measured. FIG. 4 shows the circle plots of TW signals in the case of boron. Compared to the case of Arsenic, the ion damage induced by Boron ions is more complicated. Below 5 keV ion energies it becomes nearly impossible to distinguish between the dose and energy using a TW circle plot.

Figure 5:
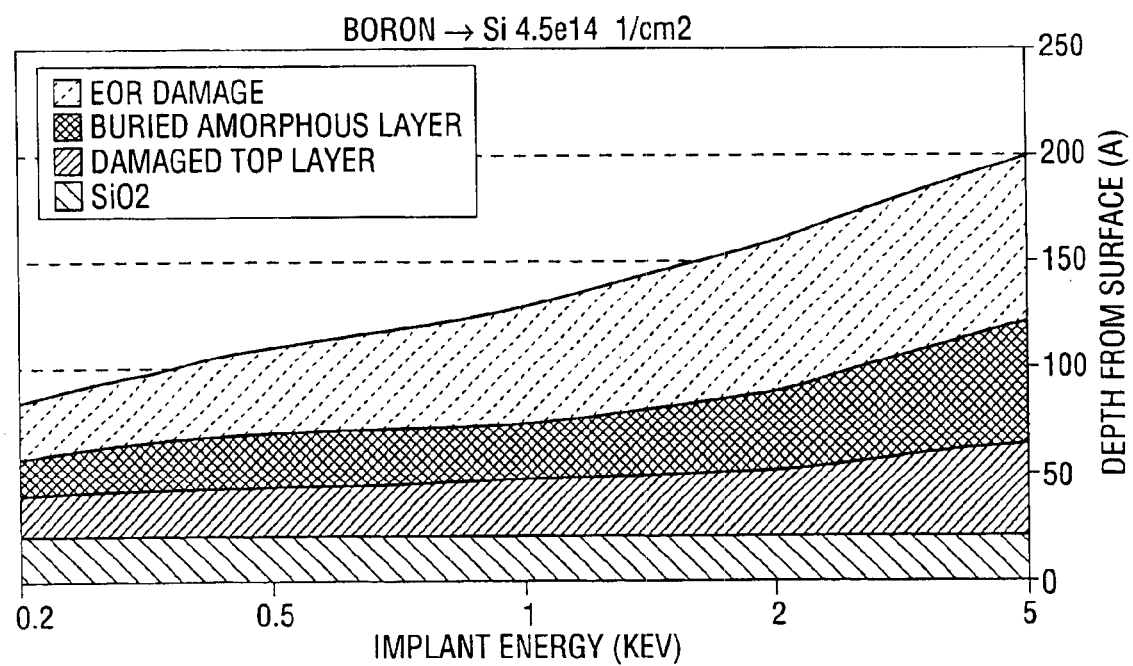
FIG. 5 illustrates the depth profile of boron ion induced crystalline damage as a function of implant energy as deduced from the spectroscopic measurements.

The spectroscopic data of Boron implants were analyzed to study the damage structure. A single damage layer model was not sufficient to explain the complicated changes in the UV part of the spectrum as a function of implant energy and dose. The sharp features developing in this region could only be explained by the interference of light reflection from several damage layers. The best fits were obtained by assuming a native oxide layer capping a damaged top layer with close to crystalline silicon dispersion, a more amorphous buried layer, and another slightly damaged layer to represent the so called end of range damage (EOR). To avoid using a separate recipe for the high energy (>2 keV) implants, a dynamic solution was sought that allows the simultaneous fit of the optical dispersion of the EOR damage layer and the thickness of the four layers. Examples of the curve fitting results for the thickness values are presented in Table III and FIG. 5.

Table III illustrates the results of curve fitting of the spectroscopic data for a series of implant energies for B$^+$ dose of 4.5e14 1/cm$^2$. The layer thickness and the 1–σ limit of a 30 point precision measurement are given in angstroms for the four layers t1=oxide, t2=top damage layer, t3=buried amorphous layer, t4=EOR damage.

TABLE III

| Wafer | Energy (keV) | t1 (Å) | 1σ-t1 (Å) | t2 (Å) | 1σ-t2 (Å) | t3 (Å) | 1σ-t3 (Å) | t4 (Å) | 1σ-t4 (Å) |
|---|---|---|---|---|---|---|---|---|---|
| 7 | 5 | 20.1 | 0.08 | 44.41 | 0.06 | 55.53 | 0.07 | 79.31 | 0.23 |
| 12 | 2 | 20.3 | 0.1 | 31.23 | 0.05 | 35.87 | 0.06 | 72.12 | 0.13 |
| 14 | 1 | 20.1 | 0.01 | 27.49 | 0.05 | 23.97 | 0.06 | 55.63 | 0.18 |
| 1 | 0.5 | 20.1 | 0.01 | 24.23 | 0.02 | 23.72 | 0.03 | 41.93 | 0.07 |
| 21 | 0.2 | 20.3 | 0.76 | 20.01 | 0.97 | 16.69 | 1.52 | 27.57 | 1.27 |

The detectability results of Table IV illustrate the difficulty in determining the boron implant energy and dose simultaneously with either the spectroscopic or the thermal wave method. The results suggest that by combining the TW and the damage layer thickness data it is possible to distinguish the energy and the dose.

Figure 6:
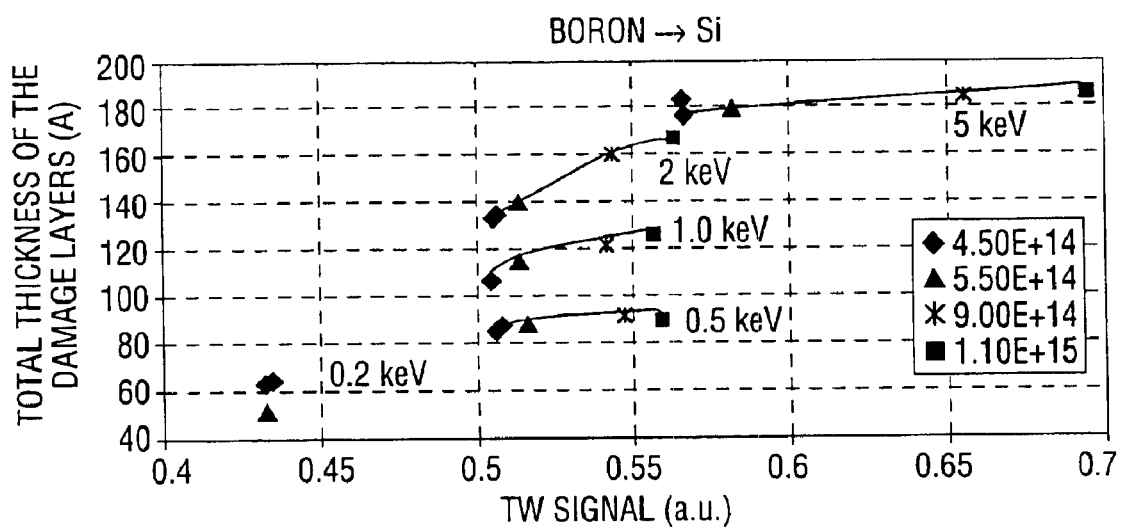
FIG. 6 is a circle plot of the combined spectroscopic and thermal wave data for the boron shallow junction implants.

The circle plot in FIG. 6 demonstrates how the thermal wave data together with the spectroscopic data provide enough information to determine the dose and energy of a particular shallow junction boron implant.

Table IV illustrates the detection of energy and dose of the Boron implanted ultra shallow junctions using the spectroscopic and thermal wave methods. 'n/a' indicates that the data was not conclusive i.e. the 30 point precision statistics was not enough to distinguish between the cases.

TABLE IV

| Parameter | Condition | Thermal wave | | Spectroscopy | |
|---|---|---|---|---|---|
| Dose-range | Energy (keV) | S (%-per-%) | DL (%-dose) | S (%-per-%) | DL (%-dose) |
| 4.5e14–1.1e15 | 5.0 | 0.1881 | 2.52 | n/a | n/a |
| 4.5e14–1.1e15 | 2.0 | 0.1261 | 4.92 | 0.1982 | 3.87 |
| 4.5e14–1.1e15 | 1.0 | 0.1144 | 2.62 | 0.2047 | 5.02 |
| 4.5e14–1.1e15 | 0.5 | 0.1043 | 2.66 | n/a | n/a |
| 4.5e14–5.5e14 | 0.2 | n/a | n/a | 0.5065 | 7.39 |
| Energy-range | Dose (1/cm$^2$) | S (%-per-%) | DL (%-energy) | S (%-per-%) | DL (%-energy) |
| 0.2–5 keV | 4.50E+14 | n/a | n/a | 0.3394 | 3.96 |
| 0.2–5 keV | 5.50E+14 | n/a | n/a | 0.3133 | 3.43 |
| 0.5–5 keV | 9.00E+14 | n/a | n/a | 0.2503 | 3.00 |
| 0.5–5 keV | 1.10E+15 | n/a | n/a | 0.2371 | 6.24 |

When combining the thermal wave damage quantity and the spectroscopic damage depth data we can estimate the detectability of the combined method to have the TW detectability for implant dose and the spectroscopic detectability for implant energy. Thus, from Table IV we get 2–5% dose detection limit and 3–7% energy detection limit for boron ultra shallow junctions with the combined technology approach.

In summary, we have described a method of determining the ion implant energy and dose simultaneously for ultra shallow junction applications by combining the experimental information of thermal wave and spectroscopic measurements. This and similar ways of combining the crystalline damage data of thermal wave measurements with the damage depth profile data from spectroscopic analysis can be used for a wide range of applications where thermal wave methods alone have been found insufficient.

While the subject invention has been described with reference to a preferred embodiment, various changes and modifications could be made therein, by one skilled in the art, without varying from the scope and spirit of the subject invention as defined by the appended claims. For example, and as noted above, thermal wave measurements are not limited to monitoring the modulated reflectivity of the sample. Alternate techniques include the measurement of the angular deviations of the probe beam, interferometric techniques and modulated spectroscopy. (See for example, U.S. Pat. No. 5,298,970 incorporated herein by reference.) In addition, there are some related techniques, which include monitoring stress pulses or acoustic waves, that could also be applied to the subject invention. All of these techniques have in common the use of a pulsed pump beam to excite the sample and a separate probe beam for investigating the effects of the pump. Those devices are also with the broad scope of the subject invention. Such systems are described in U.S. Pat. Nos. 4,710,030 and 6,081,330, also incorporated by reference. Further, it is within the scope of the subject invention to obtain additional independent measurements and combine the data generated therefrom to improve the accuracy of the result.

We claim:

1. A method for evaluating characteristics of the ion implantation in a shallow junction formed on a semiconductor sample comprising the steps of:

measuring the sample response to a periodic excitation using an optical probe and generating first output signals;

measuring the response of the sample to reflected light from a broad band wavelength source by analyzing the change in either magnitude or phase of the light induced by reflection off the surface of the sample and generating a plurality of second output signals corresponding to different wavelengths; and determining the energy and dose of the implant used to create the shallow junction using an algorithm which simultaneously regresses data corresponding to a combination of both the first and second output signals.

2. A method as recited in claim 1, wherein the first output signals are used primarily to determine the extent of the damage caused by the ion implantation while the second output signals are used primarily to determine the depth of the damage caused by the ion implantation.

3. A method as recited in claim 1, wherein the second output signals corresponding to a plurality of wavelengths are generated simultaneously.

4. A method as recited in claim 1, wherein the sample is measured with another optical probe and third output signals are generated in response thereto and the concentration of the ion implantation and the energy of the implant is evaluated based on a combination of the first, second and third output signals.

* * * * *